US012104772B1

(12) United States Patent
Heegaard et al.

(10) Patent No.: US 12,104,772 B1
(45) Date of Patent: Oct. 1, 2024

(54) SANITATION CONTROL FOR HEADLAMPS HAVING VARIABLE BEAM ILLUMINATION

(71) Applicant: Enova Illumination, Inc., Minneapolis, MN (US)

(72) Inventors: Roger W. Heegaard, Minneapolis, MN (US); Steve Scott Green, Savage, MN (US); Jordyn Kaufer, Cottage Grove, MN (US); Jeremy Ward, Brooklyn Park, MN (US)

(73) Assignee: Enova Illuminations, Inc., Minneapolis, MN (US)

( * ) Notice: Subject to any disclaimer, the term of this patent is extended or adjusted under 35 U.S.C. 154(b) by 0 days.

(21) Appl. No.: 18/413,821

(22) Filed: Jan. 16, 2024

(51) Int. Cl.
| F21V 21/084 | (2006.01) |
| A61L 2/20 | (2006.01) |
| F21V 5/04 | (2006.01) |
| F21V 29/67 | (2015.01) |
| F21V 29/70 | (2015.01) |
| F21W 131/20 | (2006.01) |
| F21Y 115/10 | (2016.01) |

(52) U.S. Cl.
CPC ............. *F21V 21/084* (2013.01); *A61L 2/20* (2013.01); *F21V 5/04* (2013.01); *F21V 29/67* (2015.01); *F21V 29/70* (2015.01); *A61L 2202/24* (2013.01); *F21W 2131/20* (2013.01); *F21Y 2115/10* (2016.08)

(58) Field of Classification Search
CPC .......... F21V 21/084; F21V 5/04; F21V 29/67; F21V 29/70; A61L 2/20; A61L 2202/24; F21W 2131/20; F21Y 2115/10
See application file for complete search history.

(56) References Cited

U.S. PATENT DOCUMENTS

| 7,210,810 B1 | 5/2007 | Iversen et al. |
| 8,047,684 B2 | 11/2011 | Chang |
| 8,662,709 B2 | 3/2014 | Chang |
| 9,234,653 B2 | 1/2016 | Ferguson |
| 9,351,799 B2 | 5/2016 | Ferguson |
| 9,494,299 B2 | 11/2016 | Chang |
| 9,687,314 B2 | 6/2017 | Ferguson |
| 10,107,483 B2 | 10/2018 | Oren |
| 10,174,912 B1 | 1/2019 | Ferguson |
| 10,441,378 B2 | 10/2019 | Ferguson |
| 10,690,325 B2 | 6/2020 | Ferguson et al. |

(Continued)

FOREIGN PATENT DOCUMENTS

| DE | 19722191 B4 * | 7/2005 | ......... G02B 19/0028 |
| WO | WO-02101283 A2 * | 12/2002 | ............... F21V 9/04 |

*Primary Examiner* — Zheng Song
*Assistant Examiner* — Glenn D Zimmerman
(74) *Attorney, Agent, or Firm* — Dietz Law Office LLC

(57) ABSTRACT

A headlamp apparatus is described that is suitable for use by health care providers. The apparatus is directed to a headlamp that provides the ability for a user to block contaminants from entering into an internal portion or cavity of the headlamp while also providing the user the ability to sanitize the internal components of the headlamp without disassembly. The apparatus is further directed to a headlamp having an actuatable iris and associated lens whereby continuous enlarging of a diameter of an aperture of the iris continuously, linearly actuates the lens away from the iris and continuously reducing the diameter of the aperture of the iris continuously, linearly actuates the lens towards the iris.

20 Claims, 15 Drawing Sheets

(56) References Cited

U.S. PATENT DOCUMENTS

| | | | |
|---|---|---|---|
| 10,767,840 B2 | 9/2020 | Ferguson | |
| 10,864,058 B2 | 12/2020 | Eddy | |
| 10,869,733 B2 | 12/2020 | Learn | |
| 11,154,880 B2 | 10/2021 | Duffin et al. | |
| 11,160,632 B1 * | 11/2021 | Ferguson | G02B 19/0028 |
| 11,478,325 B2 | 10/2022 | Learn | |
| 11,555,604 B2 | 1/2023 | Schreiber | |
| 11,611,705 B1 | 3/2023 | Chen | |
| 11,628,233 B1 | 4/2023 | Abbari et al. | |
| 2006/0285316 A1 * | 12/2006 | Tufenkjian | A61B 90/35 |
| | | | 362/570 |
| 2007/0277294 A1 | 12/2007 | Green | |
| 2014/0334157 A1 * | 11/2014 | Ferguson | F21V 21/084 |
| | | | 362/277 |
| 2014/0334159 A1 * | 11/2014 | Ferguson | A61B 90/30 |
| | | | 362/311.09 |
| 2016/0123563 A1 * | 5/2016 | Ferguson | A61B 1/0692 |
| | | | 362/277 |
| 2017/0215983 A1 * | 8/2017 | Learn | F21V 23/0414 |
| 2018/0205314 A1 | 7/2018 | Bleus et al. | |
| 2021/0299297 A1 * | 9/2021 | Roeder, Jr. | F21V 21/084 |
| 2021/0329998 A1 | 10/2021 | Crooks et al. | |
| 2021/0386141 A1 | 12/2021 | Chen | |
| 2021/0402040 A1 | 12/2021 | Botts | |
| 2021/0403725 A1 | 12/2021 | Dousset et al. | |
| 2022/0072345 A1 | 3/2022 | Viles et al. | |
| 2022/0152431 A1 | 5/2022 | Iaquinto et al. | |
| 2022/0249884 A1 | 8/2022 | Rathburn | |
| 2023/0013857 A1 | 1/2023 | Learn | |

\* cited by examiner ial # US 12,104,772 B1

SANITATION CONTROL FOR HEADLAMPS HAVING VARIABLE BEAM ILLUMINATION

CROSS-REFERENCE TO RELATED APPLICATIONS

Not Applicable

FEDERALLY SPONSORED RESEARCH AND DEVELOPMENT

Not Applicable.

JOINT RESEARCH AGREEMENT

Not Applicable.

TECHNICAL FIELD

This invention pertains generally to a headlamp that includes an actuatable iris and an associated linearly actuatable lens whereby continuous enlarging of a diameter the iris aperture continuously, linearly actuates the lens away from the iris and continuously reducing the diameter of the iris aperture continuously, linearly actuates the lens towards the iris. The present invention further pertains generally to a headlamp and system that enables a health care provider to block contaminants from entering into an internal cavity of the headlamp worn by the health care provider while also providing the ability to sanitize the internal components of the headlamp without disassembly. The headlamp of the present invention is particularly well suited for dental and surgical health care providers desiring a sanitized headlamp having the flexibility of varying the beam illumination of a focalized beam.

BACKGROUND

Over the years, various systems have been devised for illuminating a health care providers work area to increase discernability of detail in the work area and to eliminate shadows. More recently, headlamps have been utilized by doctors and other health care workers when a finite area requires concentrated illumination. In the past incandescent lights have been utilized in headlamps having a sealed housing that could be sanitized simply. However, the lumens per watt of these headlamps have proven to be a significant drain on the power supply; requiring multiple power supply replacements during extended surgical procedures. In an attempt to provide a more efficient light source having a lumen output requiring less power, light emitting diodes (LED) have been incorporated into headlamps. The LED headlamps typically have air passageways extending into the housing (rather than a sealed housing) to allow heat from the LED to escape from the housing. Further, to ensure optimal performance of the LED, fans and heatsinks are typically incorporated into the headlamp housing to draw heat away from the chip of the LED. Contaminants are able enter into the air passages, contaminating the internal components within the housing. Oftentimes all instruments, including headlamps, must be sanitized before being used by the health care provider. Rather than simply disposing of LED headlamp after use, the present invention overcomes these shortcomings by providing a filter between a cooling fan and air passageways extending into the housing, thereby inhibiting contaminants from entering into the housing. When sanitizing the headlamp of the present invention the filter may be replaced and the fan disposed of or replaced with a sanitized fan.

Other prior headlamps have attempted to provide a beam of light that is both homogenous and uniform in brightness and color from edge to edge of the beam. Although optical assemblies have been aligned with a light source within a housing of a headlamp, there remains a need for a sanitary headlamp that allows the user to vary the spot size of the beam illumination without compromising the uniformity of the beam brightness.

SUMMARY

Embodiments according to aspects of the invention provide a sanitary apparatus or headlamp assembly having an efficient light source that also includes a mechanism to vary the spot size of the illumination beam. The apparatus according to aspects of the invention generally includes a headlamp housing and a light assembly. The headlamp housing has a cavity or void that is adapted to contain the various components of the headlamp including the light assembly. The housing includes a longitudinal axis extending through the housing and the light assembly has a length axis aligned parallel with the longitudinal axis of the housing. The light assembly in accordance with these aspects of the invention includes a light source, spaced apart condenser lens, a spacer, a containment member that contains an iris member and linearly actuatable lens associated with the adjustable iris, and a front lens. The light source, two condenser lenses, spacer, iris, linearly actuatable lens, and front lens are all aligned along the length axis of the light assembly. The spacer separates the two condenser lenses. The headlamp housing further has a light emitting opening extending from an outer surface of the headlamp housing into the interior cavity wherein the center of the central opening is aligned with the longitudinal axis of the housing. The front lens is oriented and aligned proximate both the light assembly and the central opening of the housing. Light passing through the two condenser lenses, then the iris and linearly actuatable lens, and then travelling through the front lens before exiting the central opening exhibits a small spot size light beam of illumination without compromising the uniformity of the beam brightness. In certain embodiments the containment member may include an actuator mechanism that reduces and increases a diameter of the aperture of the iris in proportion to a distance the moveable lens actuates linearly.

According to other aspects of the invention the light source is comprised of a light emitting diode (LED). The LED includes a base or PCBA having a layer of copper to facilitate heat dispersion. The LED light source may further include a primary heat sink and secondary heat sink thermally coupled to the LED. The primary and secondary heat sinks are contained within the internal cavity of the headlamp housing and draw heat produced by the diode away from the LED. A replaceable fan may be adapted for circulating air within the interior cavity of the headlamp housing. A removable filter assembly is coupled between the fan and a main portion of the interior cavity of the headlamp housing. By way of example, and without limitation intended, a HEPA filter has been found to be particularly well suited for use in the filter assembly of the present invention. The filter blocks contaminants from entering the interior of the headlamp housing, thereby reducing the components and surface area required to sanitize the headlamp. Additionally, the headlamp housing may include a plurality of ports extending from the outer surface of the headlamp housing into the internal cavity. The plurality of ports are adapted and well suited for transmitting vapors into the internal cavity of the headlamp housing to sanitize the interior and components within the housing. Further, the filter assembly may include a thumb tab that extends from an external surface of the headlamp housing, providing a gripping surface for the user to pull the filter from the housing when replacing the filter. Additionally, a HEPA filter may consist of a pad capable of filtering particulate having a size greater than 03 microns and may include a scent fixed in the pad. The scent may be chosen to transmit a vapor in the air that masks the smell of cauterized blood or tissue to helps reduce potential nausea of the user. Those skilled in the art will further appreciate that the headband or comfort band of the headlamp may be impregnated, infused, dipped or otherwise treated with a compound to mask undesirable smells and reduce nausea.

Another embodiment according to aspects of the invention generally includes a headlamp housing, a fan, a removeable filter and a light assembly. The headlamp housing has an interior cavity adapted to contain components of the headlamp. The headlamp housing further has a light emitting opening extending from an outer surface of the headlamp housing into the interior cavity wherein a longitudinal axis extends through the housing and is aligned with a center of the central opening. The fan is adapted for circulating air within the interior cavity of the headlamp housing. Further, the removable filter assembly is coupled between the fan and a main portion of the interior cavity of the headlamp housing to restrict contaminants from entering the interior cavity of the headlamp housing. The light assembly has a length axis aligned parallel with the longitudinal axis of the housing. The light assembly includes an LED, multiple condenser lens, spacers, adjustable iris, linearly actuatable lens and front lens that are all aligned along the length axis of the light assembly. The first condenser lens is aligned along the length axis of the light assembly adjacent the LED. The second condenser lens is aligned along the length axis of the light assembly axially proximate the first condenser lens wherein the spacer is aligned along the length axis of the light assembly and positioned between the first condenser lens and second condenser lens. A containment member is aligned along the length axis of the light assembly wherein the containment member contains the adjustable iris member having an adjustable aperture contained therein. Further, the containment member has a linearly actuatable lens contained therein that is positioned forward the iris or on the opposite side of the iris as the condenser lenses. The front lens is aligned along the length axis of the light assembly proximate both the linearly actuatable lens and the central opening of the housing.

In accordance with other aspects of the invention this embodiment of the invention may include an LED having a PCBA with a copper layer as the base of the LED. A primary heat sink and secondary heat sink may be thermally coupled to the LED, wherein both the primary heat sink and secondary heat sink are contained within the internal cavity of the headlamp housing. The headlamp housing may also have a plurality of ports extending from the outer surface of the headlamp housing into the internal cavity. The plurality of ports may be adapted for transmitting vapors into the internal cavity of the headlamp housing. The vapors may originate from a substance that is suitable for sanitizing or cleaning components contained within the internal cavity of the headlamp housing. The HEPA filter may include a thumb tab that extends from an external surface of the headlamp housing. The thumb tab is particularly useful as a gripping surface when replacing the HEPA filter. The HEPA filter may further consists of a scented pad capable of filtering particulate having a size greater than 0.3 microns. The scent in the pad may be of the type to help reduce nausea of the health care worker wearing the headlamp. The containment member may further include a mechanism or actuator member that reduces and increases a diameter of the aperture of the iris in proportion to a distance the moveable lens actuates linearly.

In use, a health care provider may be provided with a headlamp having an adjustable light beam and having a sanitary cooling mechanism. The headlamp includes a headlamp housing, a fan, a filter, and a light source assembly. The housing has an interior cavity adapted to contain components of the headlamp, the headlamp housing further having a light emitting opening extending from an outer surface of the headlamp housing into the interior cavity, and the headlamp housing further having a longitudinal axis extending through the housing and aligned with a center of the central opening. The fan is adapted for circulating air within the interior cavity of the headlamp housing. The removable HEPA filter assembly is coupled between the fan and a main portion of the interior cavity of the headlamp housing. The light assembly is contained within the interior cavity of the headlamp housing. The light assembly has a length axis aligned parallel with the longitudinal axis of the housing. The light assembly further has an LED aligned along the length axis of the light assembly, a first condenser lens aligned along the length axis of the light assembly adjacent the LED, a second condenser lens aligned along the length axis of the light assembly axially proximate the first condenser lens wherein a spacer is aligned along the length axis of the light assembly and positioned between the first condenser lens and second condenser lens. A containment member aligned along the length axis of the light assembly contains the iris member having an adjustable aperture and further the linearly actuatable lens therein. The front lens is aligned along the length axis of the light assembly proximate both the light assembly and the central opening of the housing. The headlamp housing may further include a plurality of ports extending from the outer surface of the headlamp housing into the internal cavity, that allows a user to infuse vapors into the internal cavity of the headlamp housing wherein the vapors are suitable for sanitizing or cleaning the components contained within the internal cavity of the headlamp housing. The user may further choose to infuse an anti-microbial vapor through the plurality of ports. Further, the user may insert a filter consisting of a scented pad capable of filtering particulate having a size greater than 0.3 microns into the removable filter assembly. The user may further choose a scent that, when smelled by the healthcare worker wearing the lamp, the scent may help to reduce nausea.

The accompanying drawings, which are incorporated in and constitute a portion of this specification, illustrate embodiments of the invention and, together with the detailed description, serve to further explain the invention. The embodiments illustrated herein are presently preferred; however, it should be understood, that the invention is not limited to the precise arrangements and instrumentalities shown. For a fuller understanding of the nature and advantages of the invention, reference should be made to the detailed description in conjunction with the accompanying drawings.

DESCRIPTION OF THE DRAWINGS

In the various figures, which are not necessarily drawn to scale, like numerals throughout the figures identify substantially similar components.

DETAILED DESCRIPTION

Figure 1:
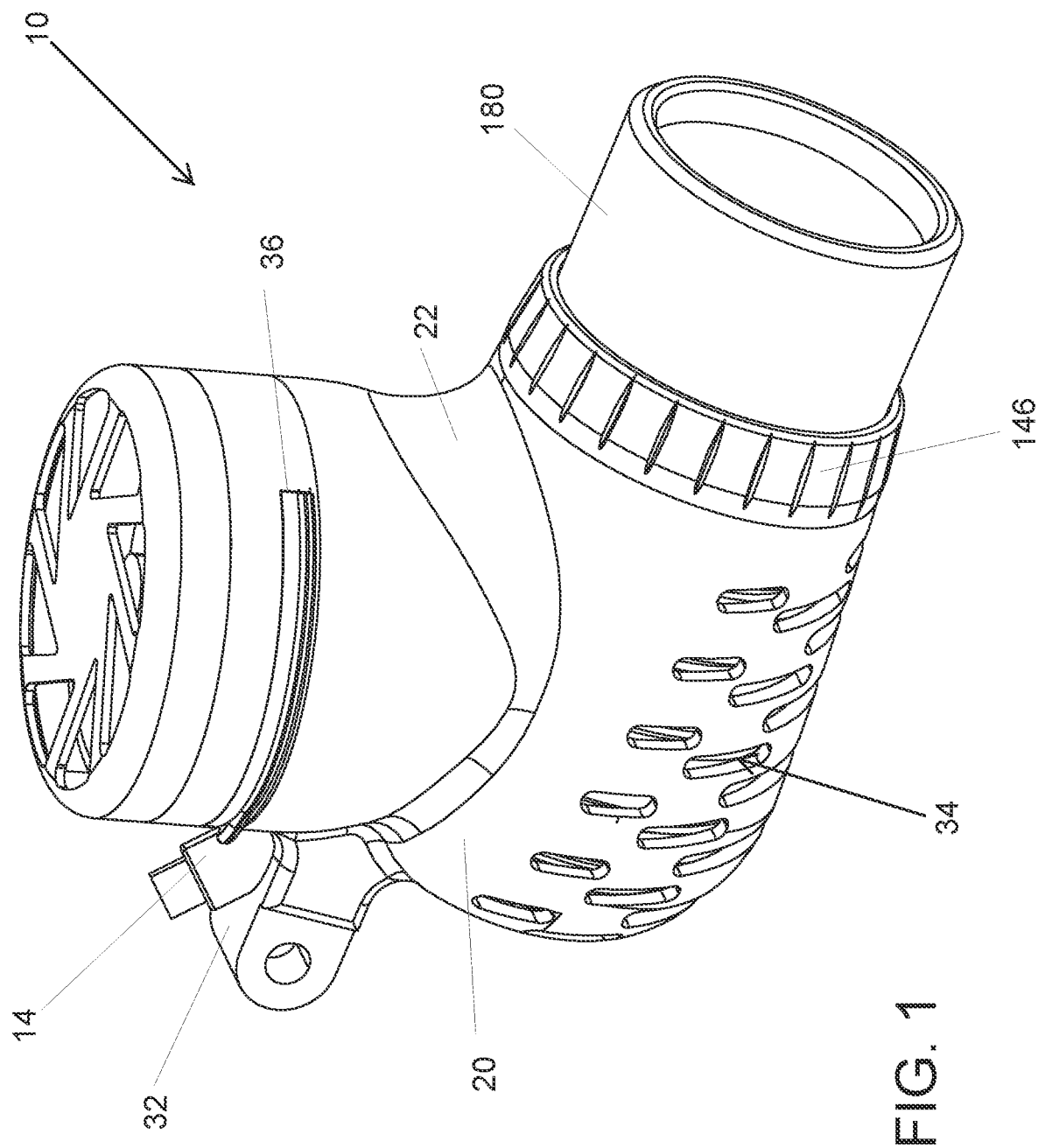
FIG. 1 is a front left upper perspective view of an embodiment of the headlamp of the present invention.

The following description provides detail of various embodiments of the invention, one or more examples of which are set forth below. Each of these embodiments are provided by way of explanation of the invention, and not intended to be a limitation of the invention. Further, those skilled in the art will appreciate that various modifications and variations may be made in the present invention without departing from the scope or spirit of the invention. By way of example, those skilled in the art will recognize that features illustrated or described as part of one embodiment, may be used in another embodiment to yield a still further embodiment. Thus, it is intended that the present invention also cover such modifications and variations that come within the scope of the appended claims and their equivalents.

The headlamp apparatus 10 of the present invention is suitable for use by health care workers and by others desiring a sanitary headlamp. An embodiment of the headlamp 10 of the present invention generally includes an external housing 20, replaceable fan assembly 40, filter assembly 60 and light assembly 100. The housing 20 includes an internal cavity 24 adapted to contain various components of the headlamp including a primary PCBA 16, primary heat sink 80 and secondary heat sink 84. Without limitation intended, the housing and various components may be made from a polymer or metal of known suitable construction. The polymer and metal may be infused, treated or coated with anti-microbial element or compound of known suitable construction. Likewise, the headband or comfort band of the headlamp may be impregnated, infused, dipped or otherwise treated with an antimicrobial or compound to mask undesirable smells and reduce nausea. Similarly, a vapor may be injected into the cavity of the housing to disinfect the internal components of the headlamp 10. Without limitation intended the antimicrobial cleansing vapor may be delivered in aerosol form through 1-way valve/connection ports and then dispersed through headlamp system. Further, the disposable replaceable filter media 66 of the filter assembly 60 may be of known suitable construction and capable of filtering particulate as specified by HEPA medical standards. By way of example and without limitation intended the filter media may be capable of trapping particulate as small as 0.3 microns including dust, pollen, mold, bacteria, and other airborne particles.

Figure 2:
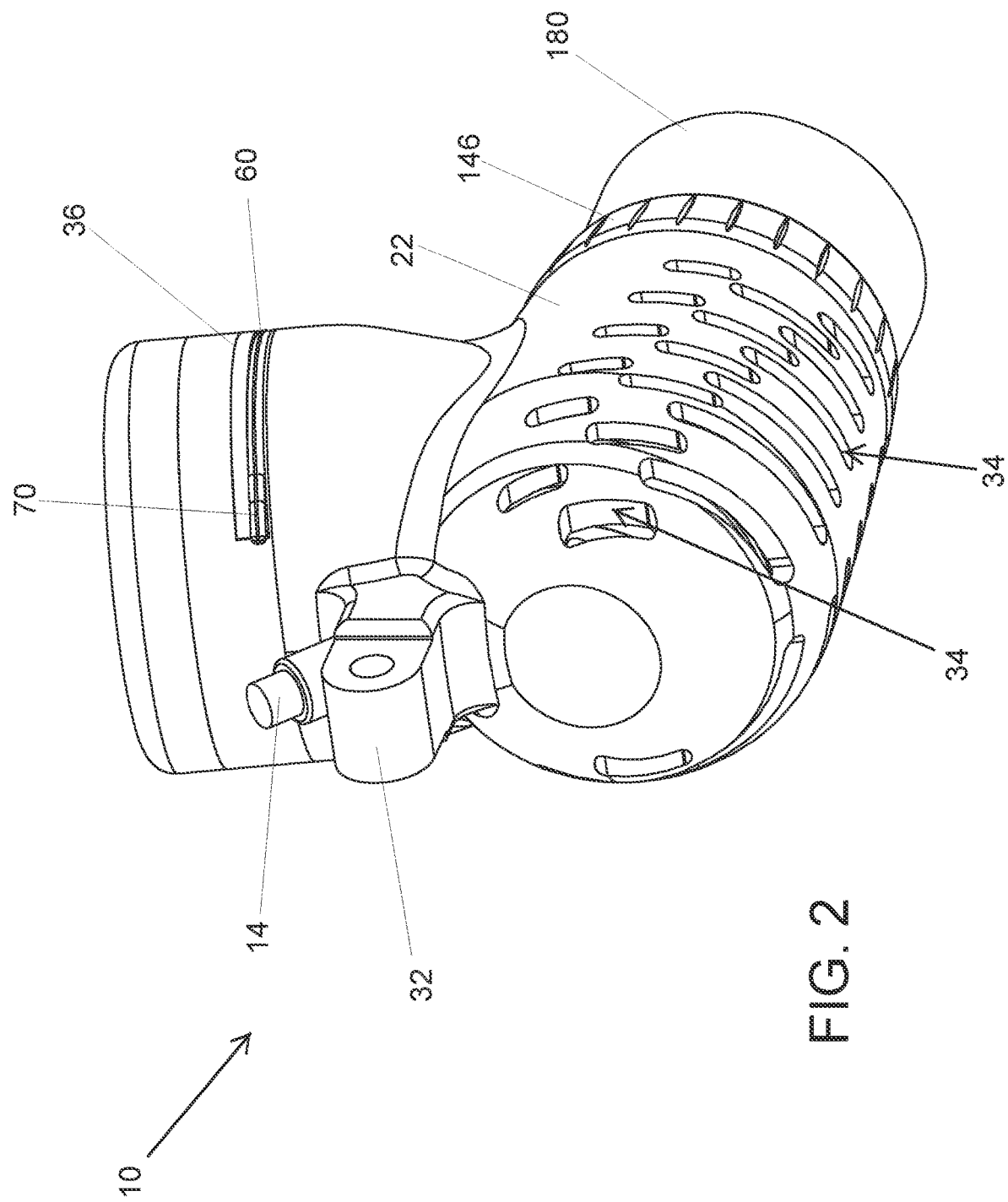
FIG. 2 is a back right upper perspective view of an embodiment of the headlamp of the present invention.
Figure 3:
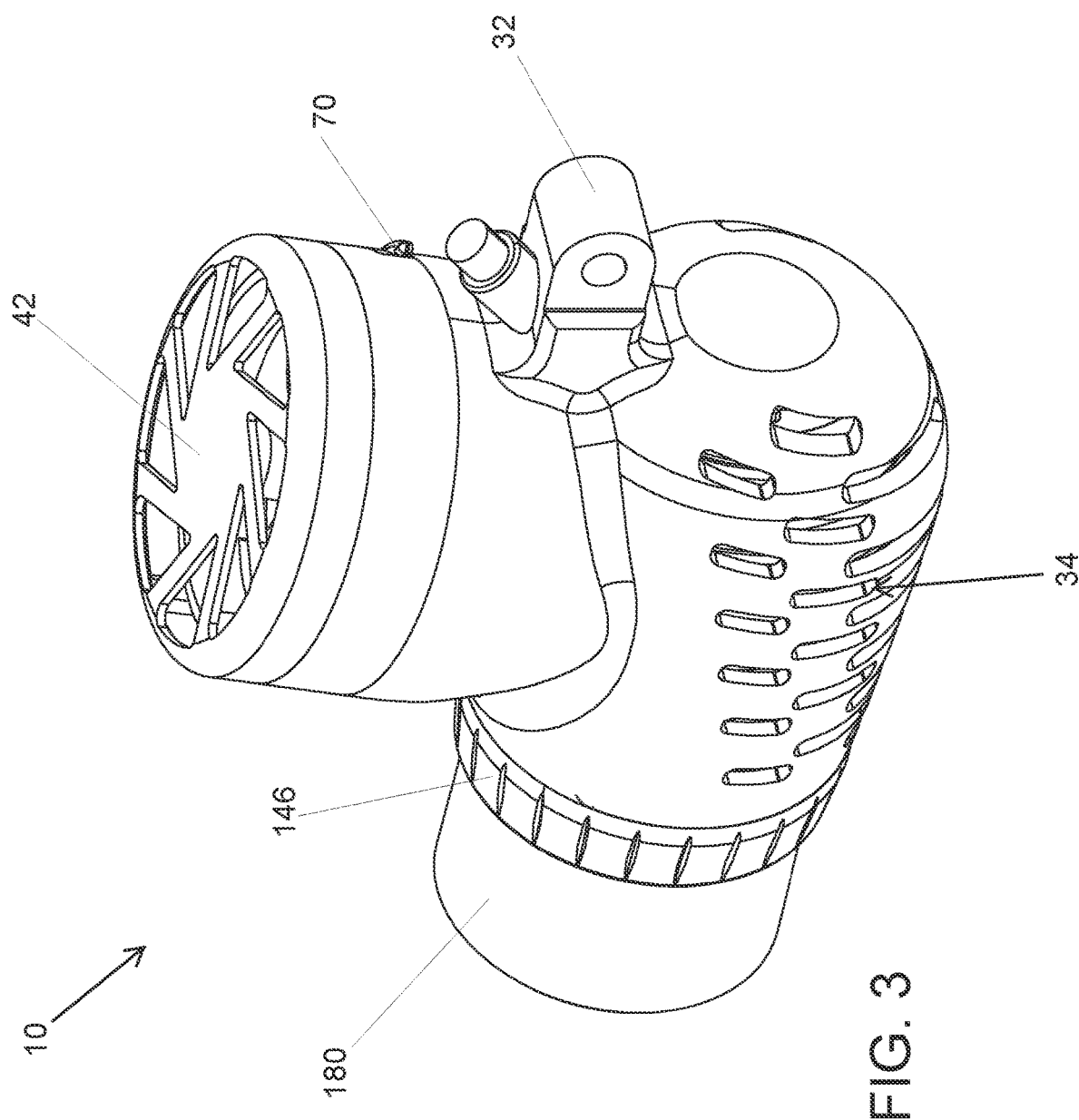
FIG. 3 is a back left upper perspective view of an embodiment of the headlamp of the present invention.
Figure 4:
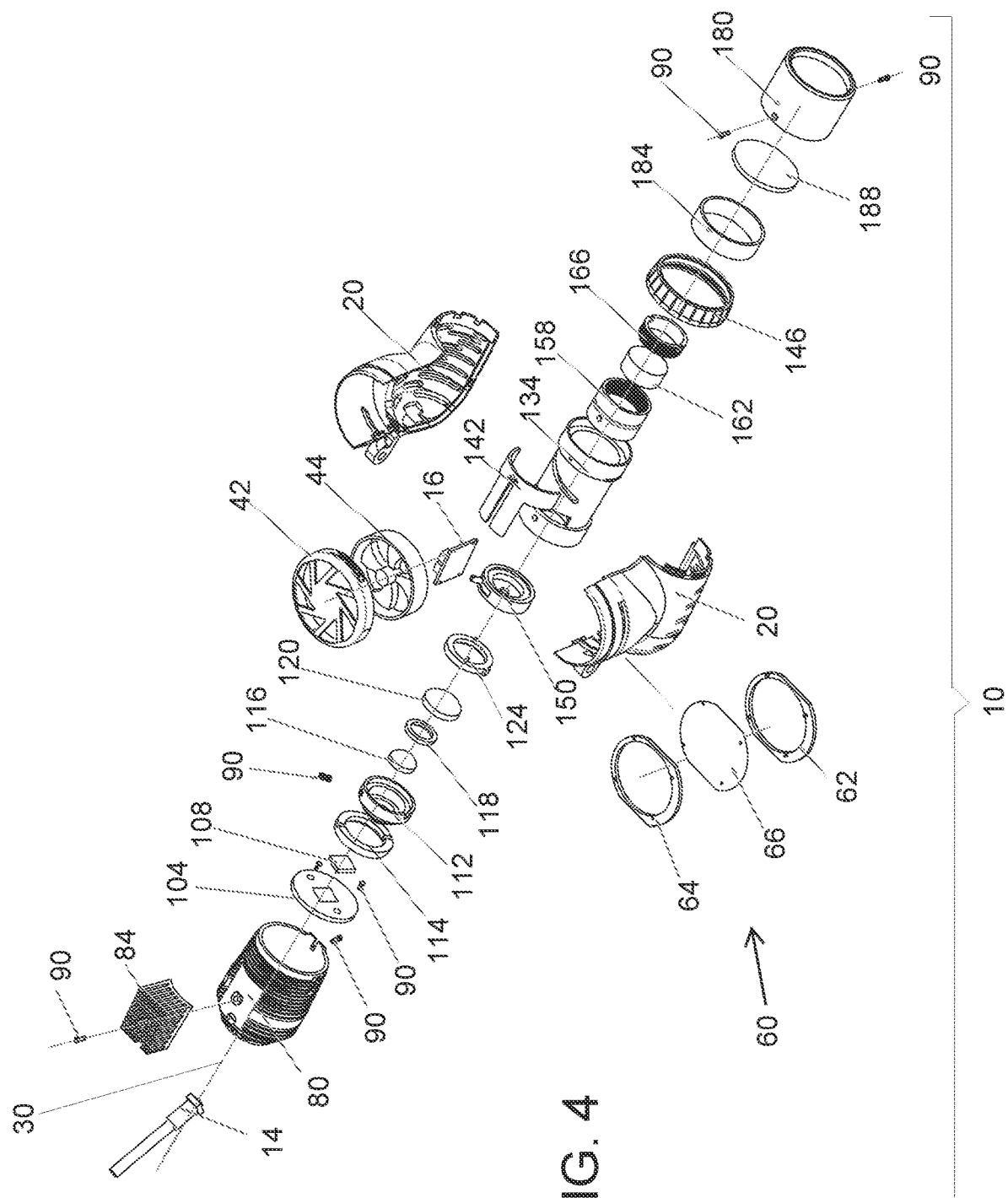
FIG. 4 is a partial exploded perspective view of an embodiment of the headlamp apparatus of the present invention.
Figure 5:
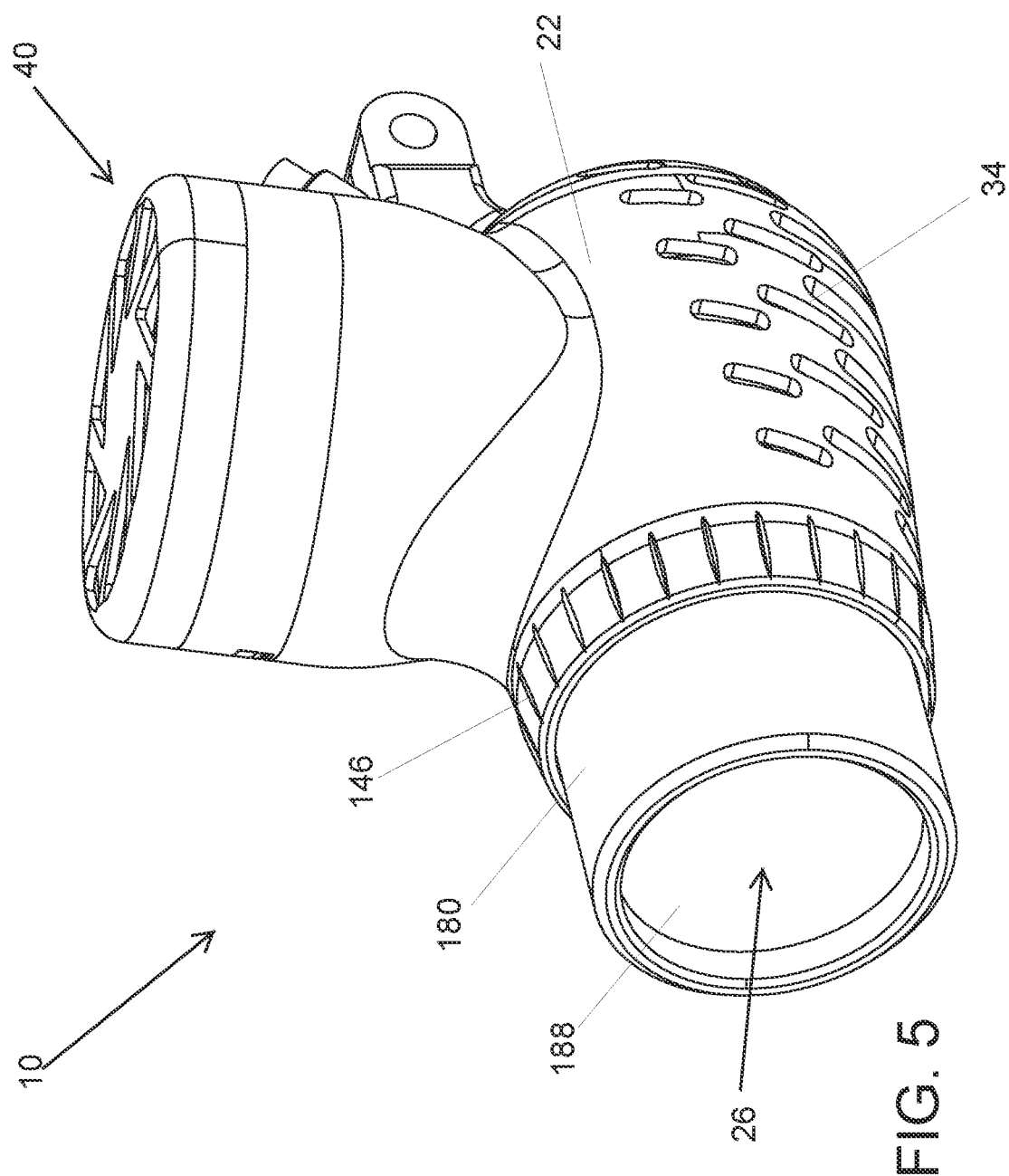
FIG. 5 is a front right upper perspective view of an embodiment of the headlamp apparatus of the present invention.
Figure 6:
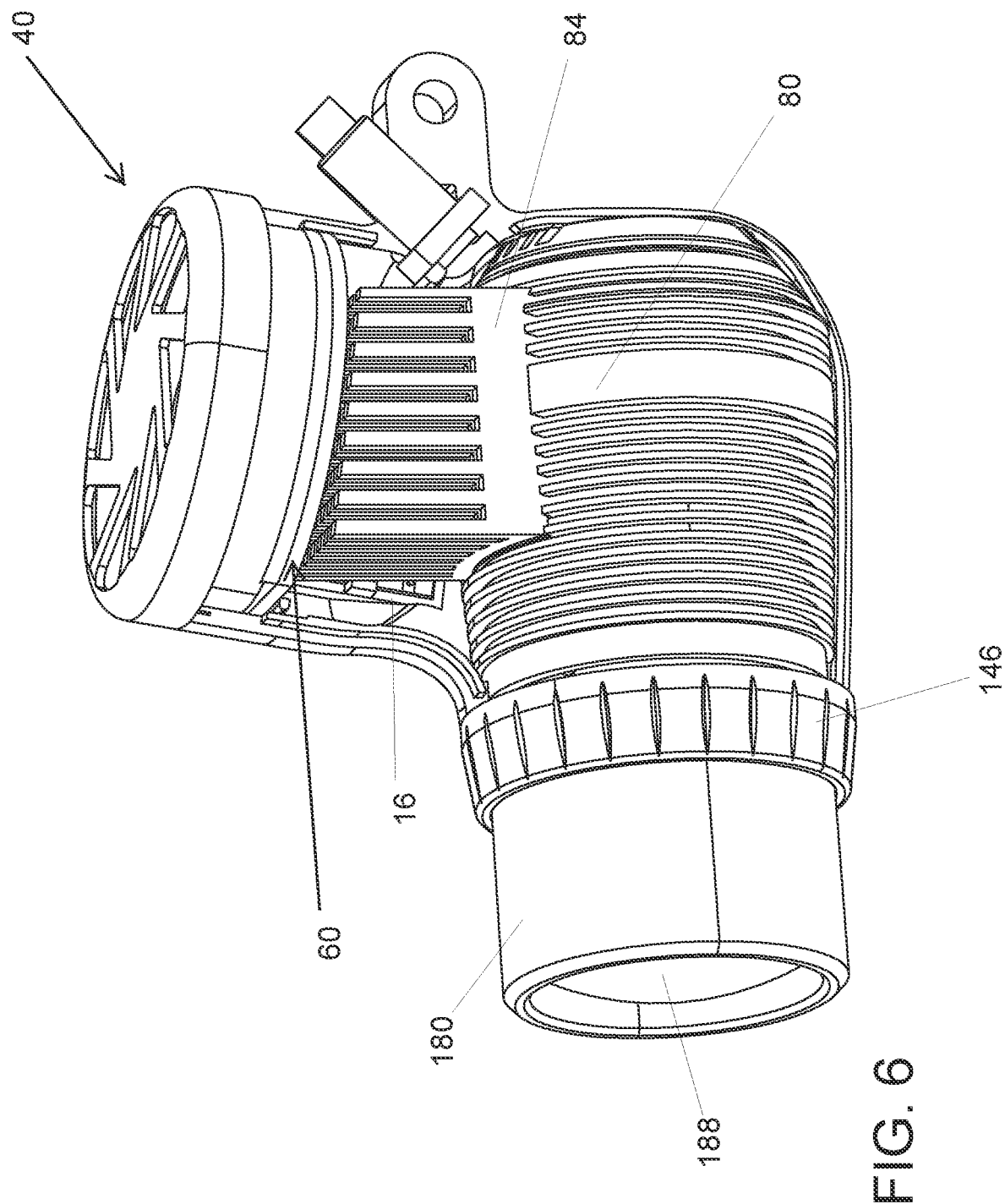
FIG. 6 is a partial sectional side perspective view of an embodiment of the headlamp apparatus, showing a secondary heat sink.
Figure 7:
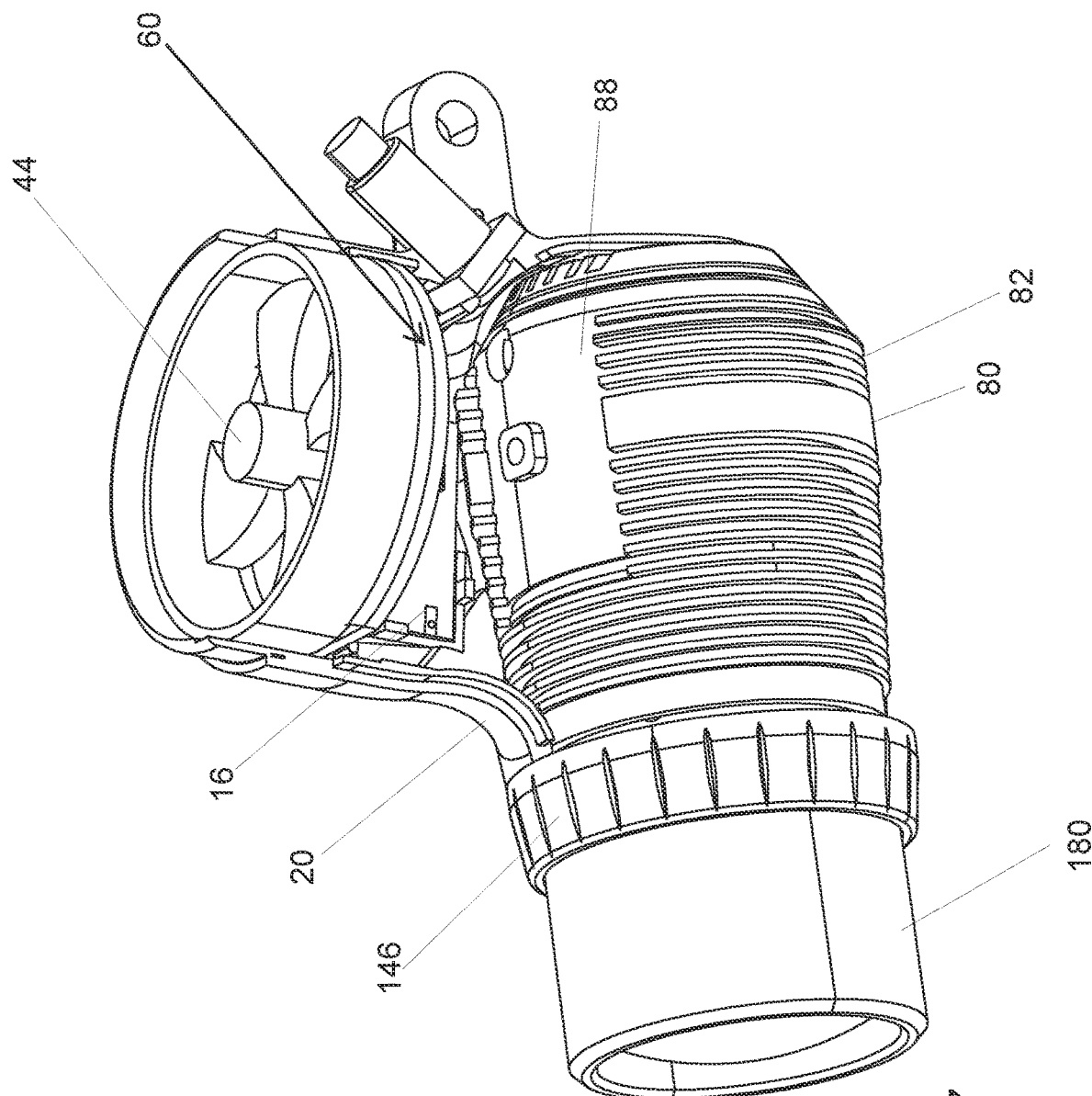
FIG. 7 is a partial sectional side perspective view of an embodiment of the headlamp apparatus of the present invention, showing the secondary heat sink removed.
Figure 8:
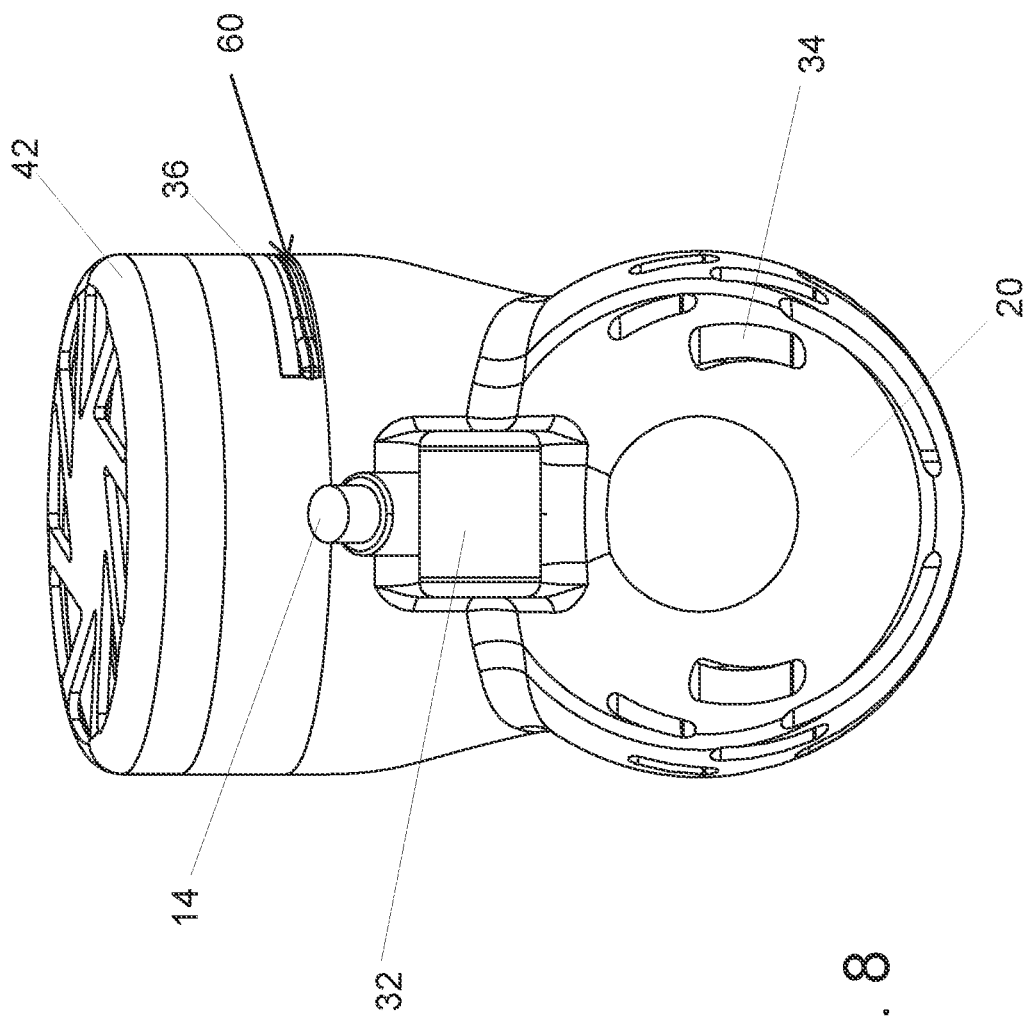
FIG. 8 is a back end perspective view of an embodiment of the headlamp apparatus of the present invention.
Figure 9:
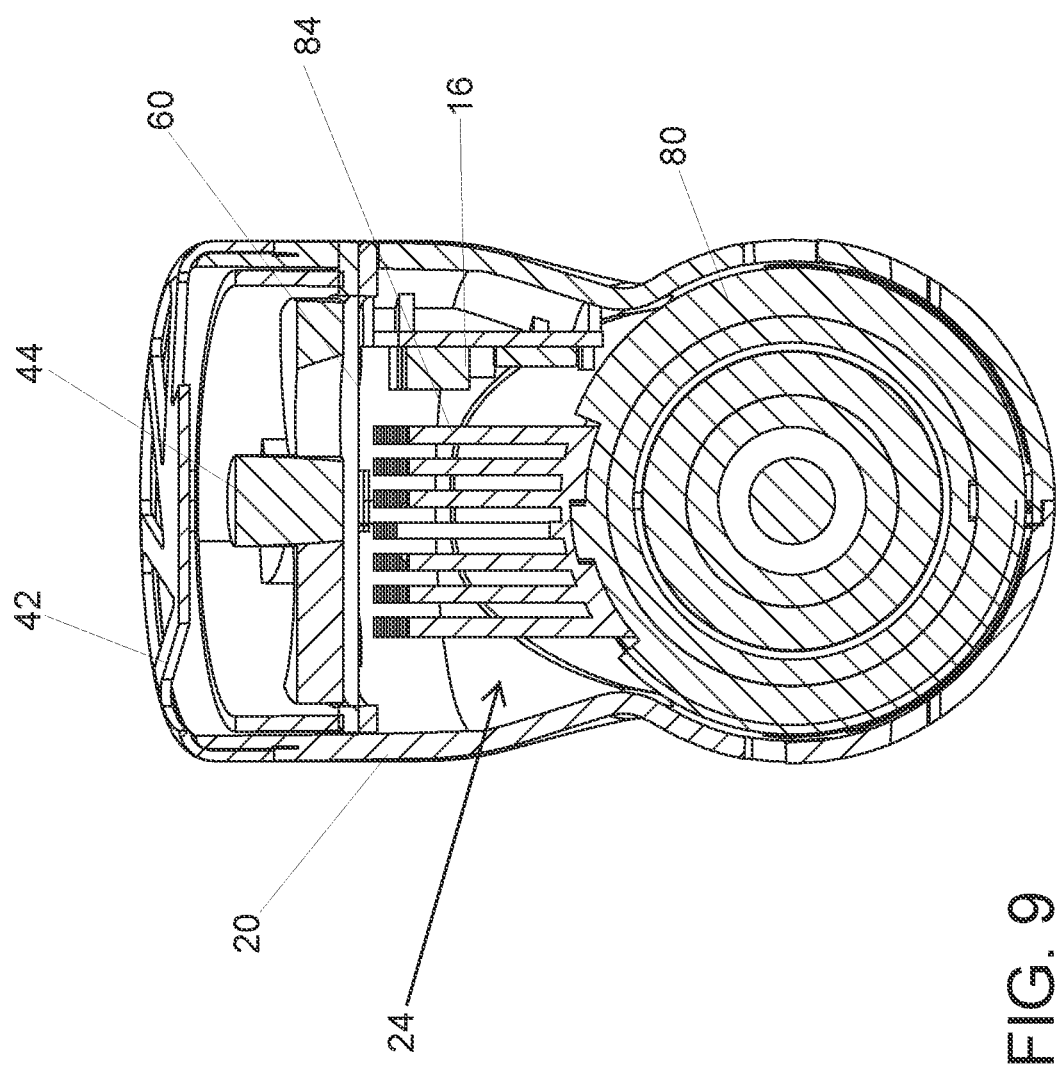
FIG. 9 is a partial sectional back end perspective view of the headlamp apparatus of the present invention.
Figure 10:
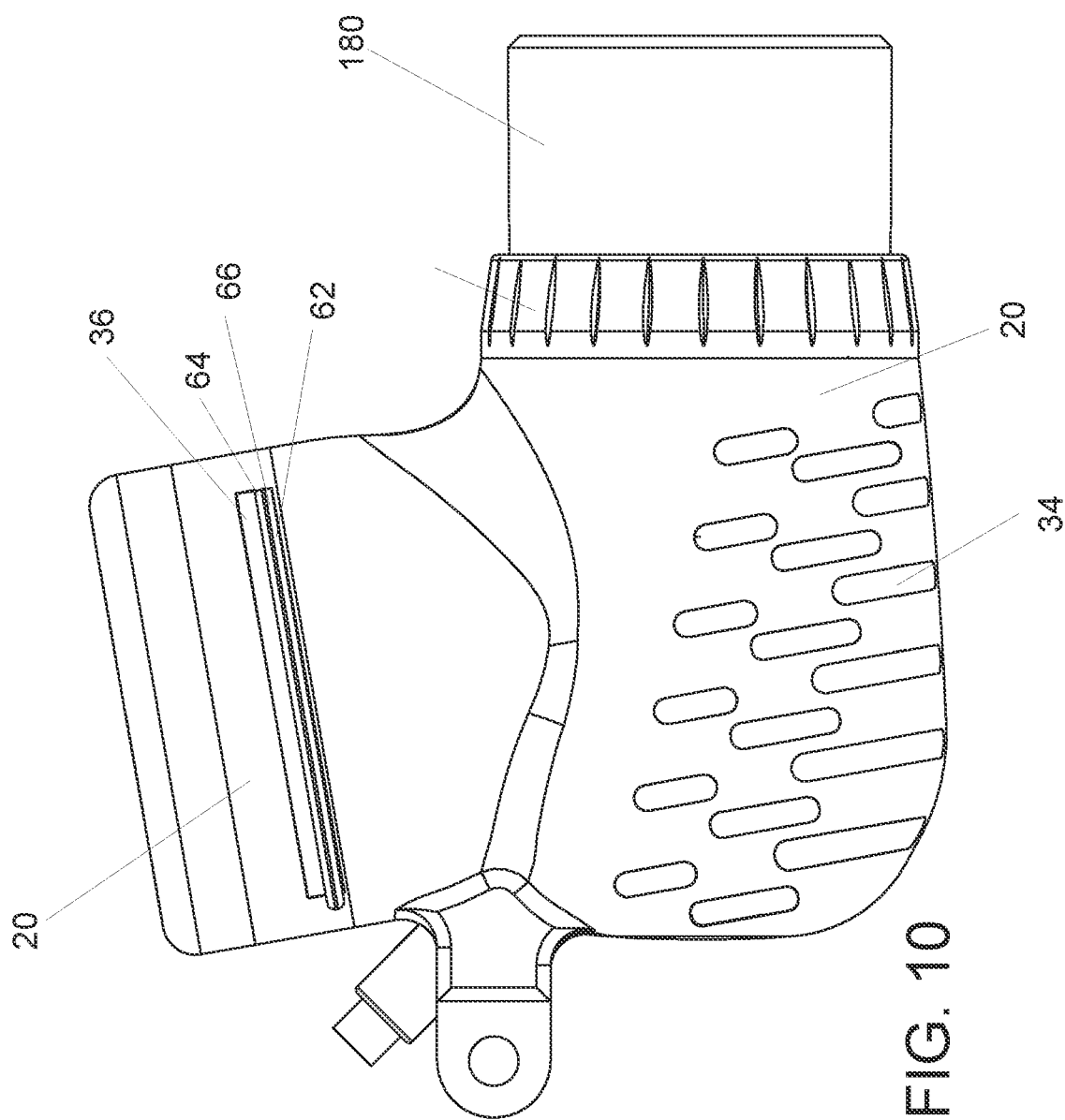
FIG. 10 is a left side perspective view of the headlamp apparatus of the present invention.
Figure 11:
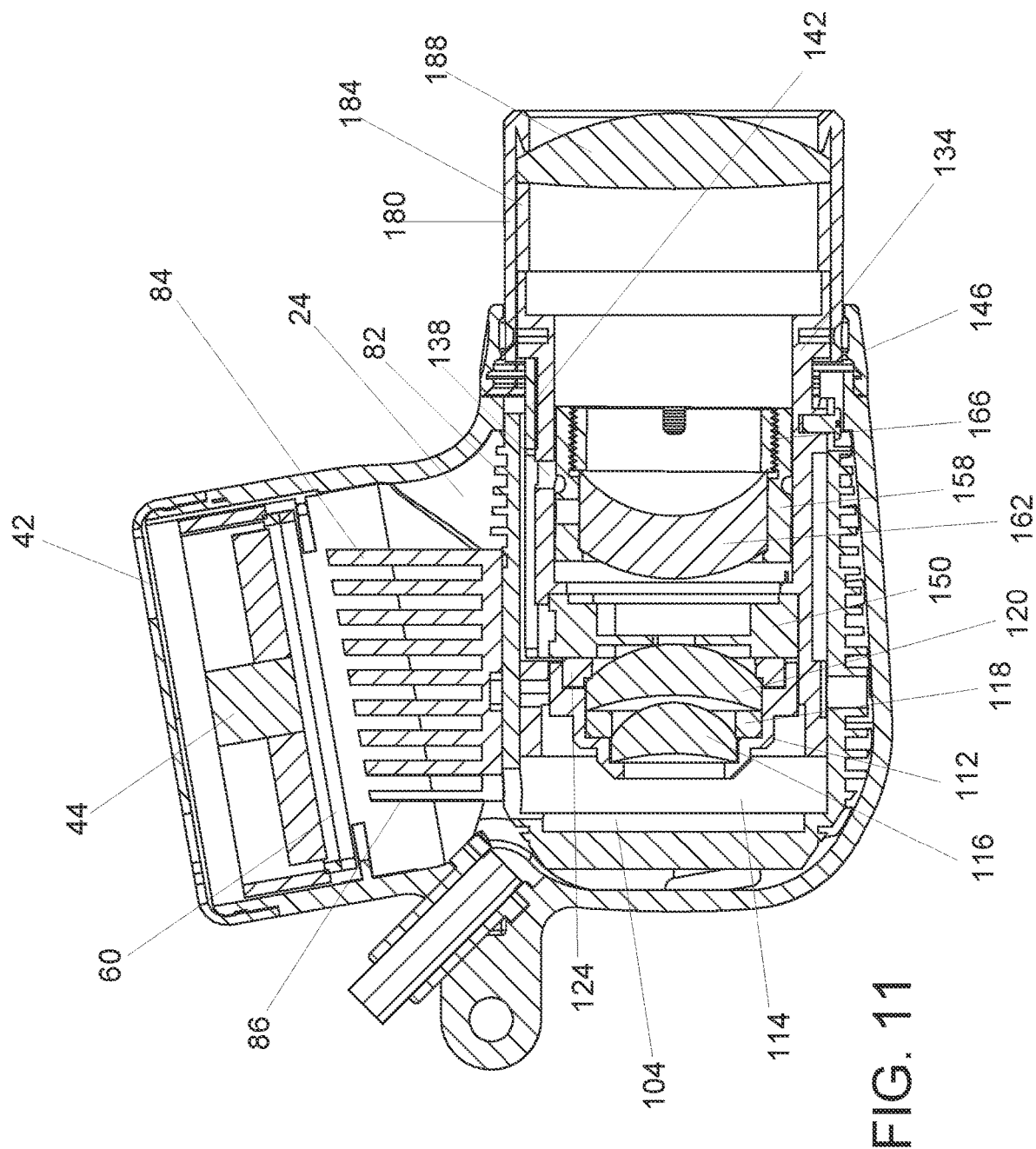
FIG. 11 is a partial sectional side perspective view of the headlamp apparatus of the type shown in FIG. 10.
Figure 12:
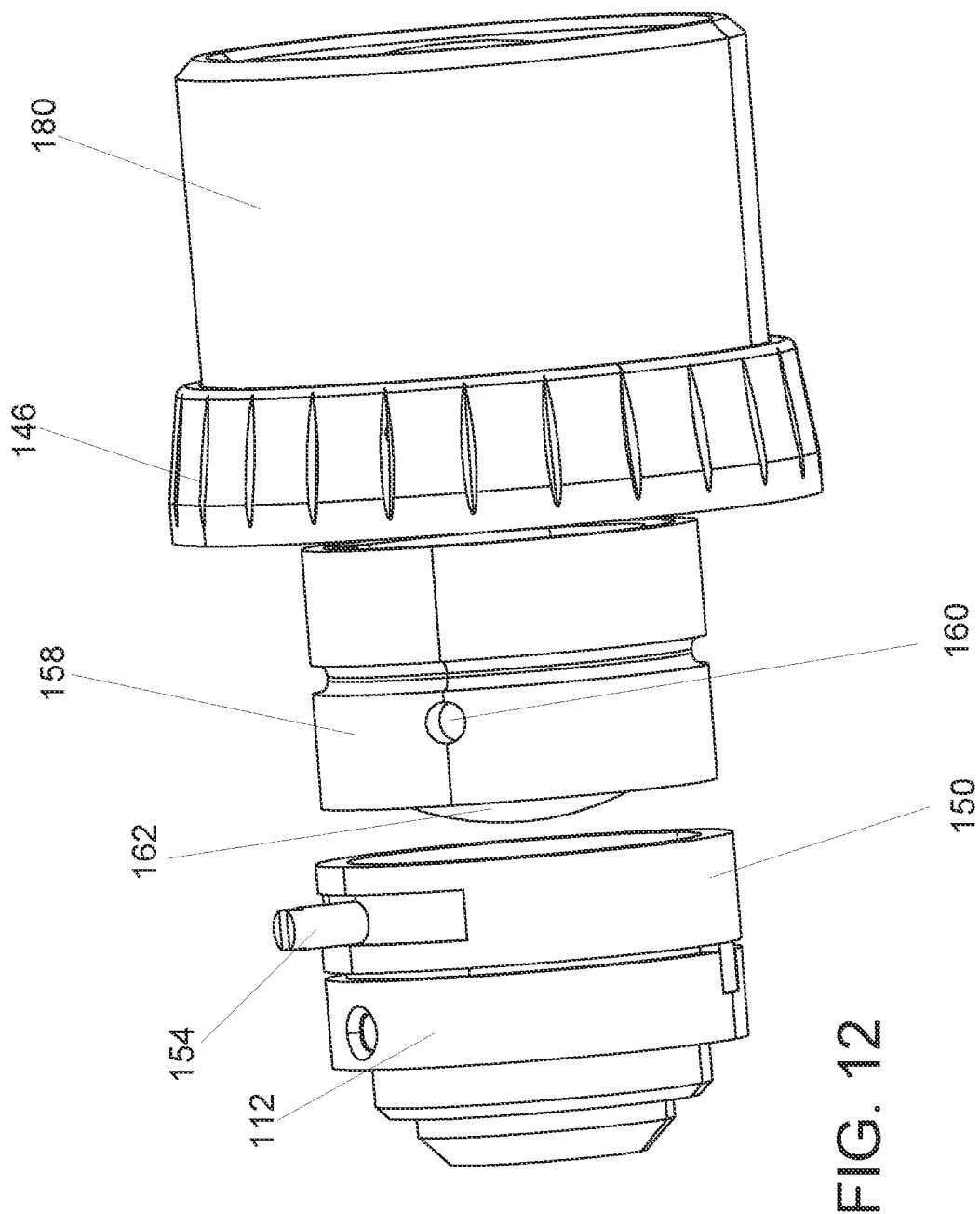
FIG. 12 is a partial sectional side perspective view of the light assembly of the headlamp apparatus in accordance with the present invention and shown having a portion of the linear actuation assembly removed.
Figure 13:
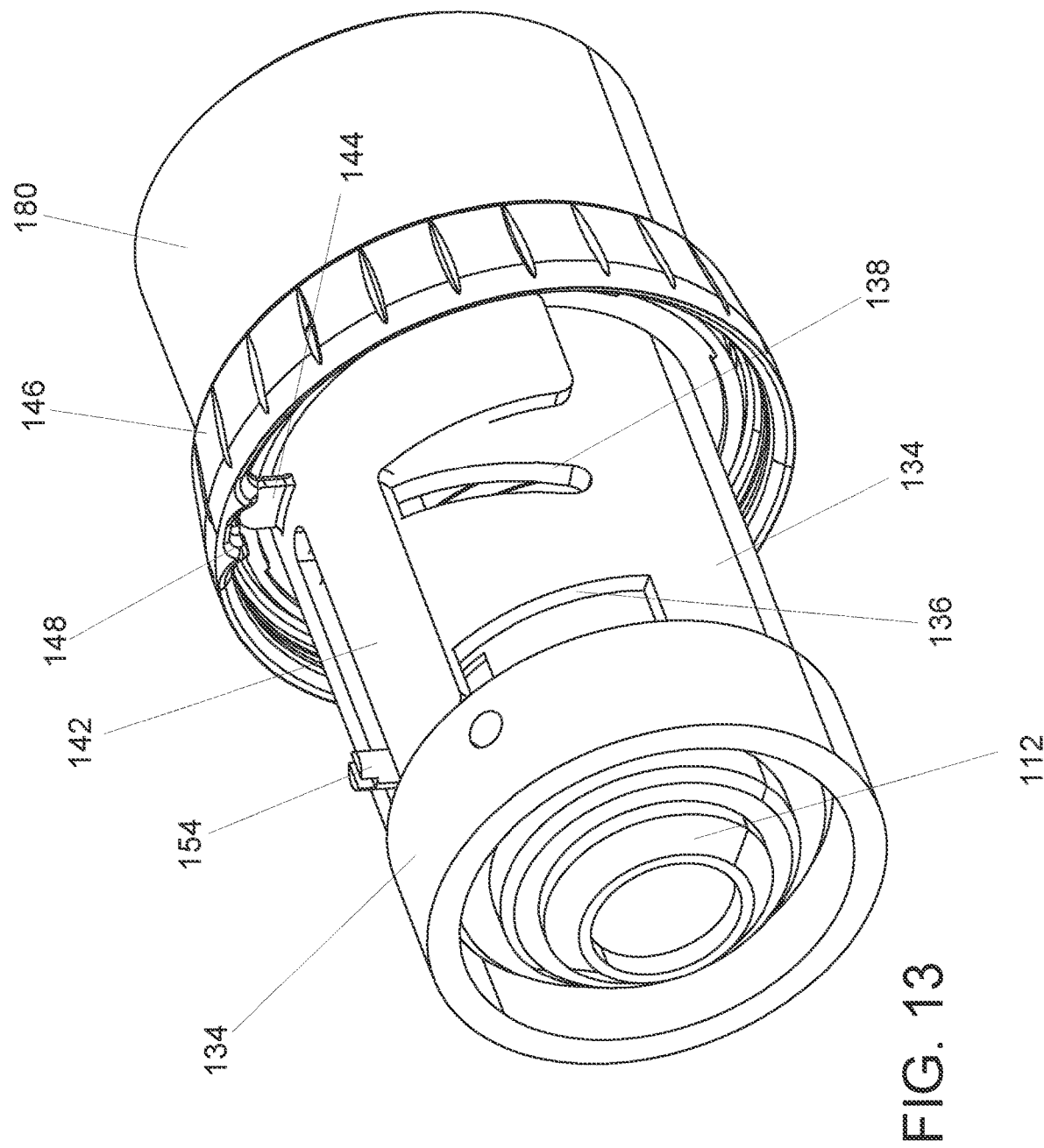
FIG. 13 is a partial sectional side perspective view of the light assembly of the headlamp apparatus in accordance with the present invention and shown having a portion of the linear actuation assembly removed.
Figure 14:
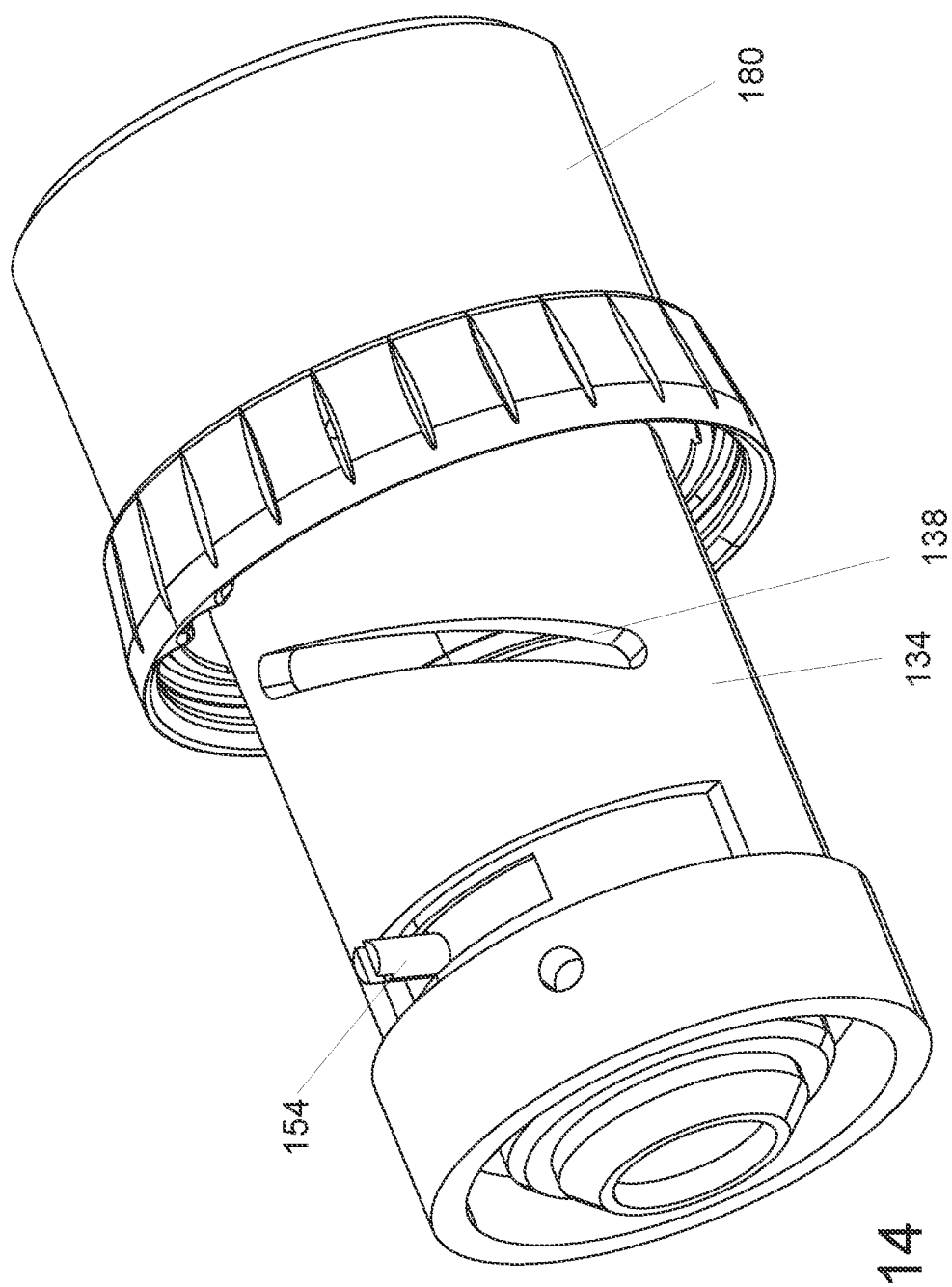
FIG. 14 is a partial sectional side perspective view of the light assembly of the headlamp apparatus in accordance with the present invention and shown having a portion of the linear actuation assembly removed.
Figure 15:
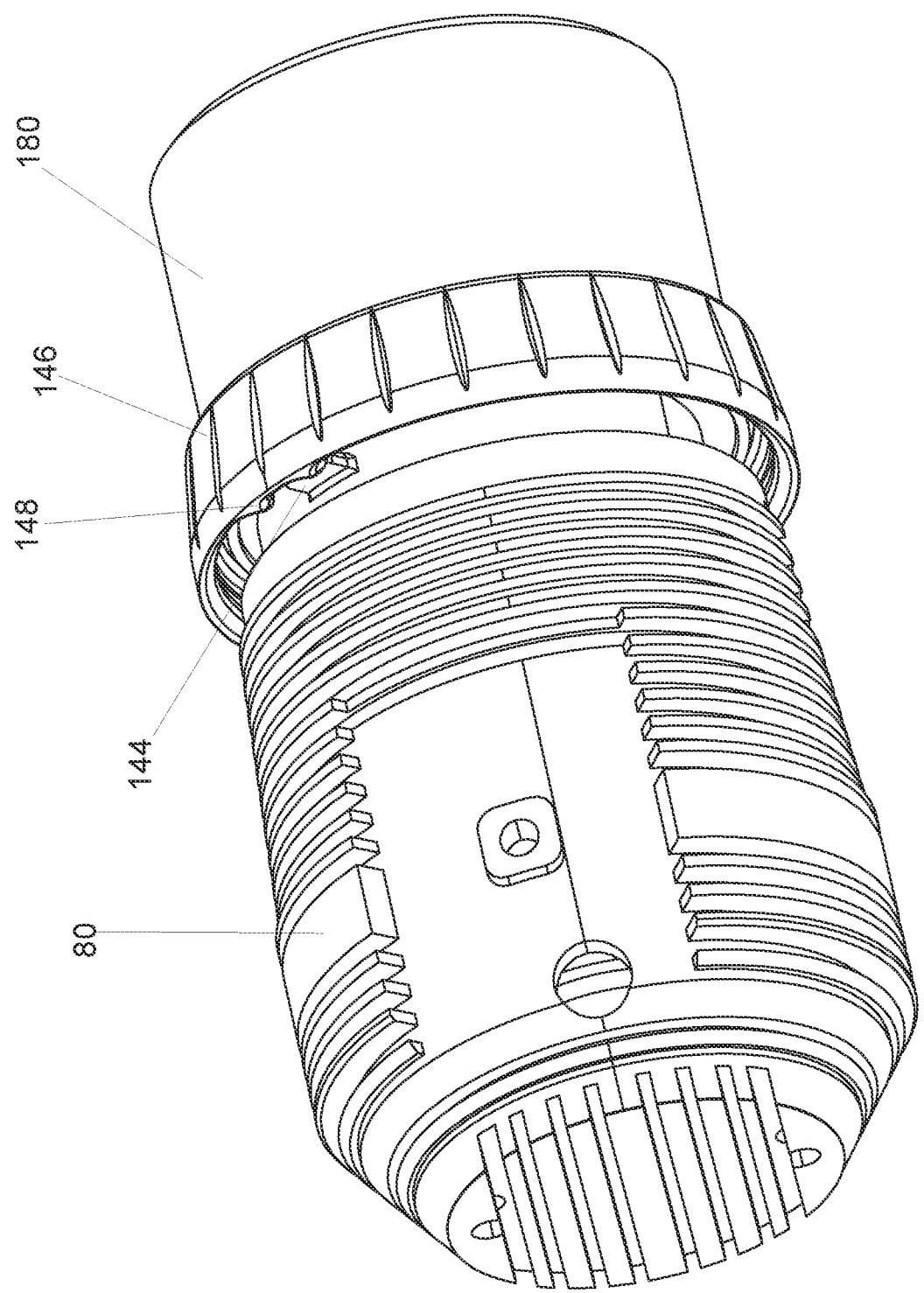
FIG. 15 is a side perspective view of the light assembly of the headlamp apparatus in accordance with the present invention.

Turning attention now to the Figures, embodiments according to aspects of the invention will now be described. Referring first to FIGS. 1-3, the headlamp 10 is shown having a housing 20, adjusting ring 146 for adjusting a spot size of the illumination beam and a front barrel 180. Power supply cable 14 extends out the housing 20. The housing has an external or outer surface 22 and a hinge attachment point 32. A central or longitudinal axis 30 of the housing 20 is identified in FIG. 4. The housing 20 further includes ports 34 extending from the outer surface 22 into the internal cavity 24 of the housing. The housing 22 further includes a slot 36 formed through the housing that is adapted for receiving the filter assembly 60. A shroud 42 of the replaceable fan assembly 40 covers a top portion of the housing. The filter assembly 60 includes a tab 70 extending from the housing 20 when the filter assembly is completely inserted into the housing. The tab 70 assists the user in removing and replacing the filter assembly 60 from the housing. In an embodiment of the invention, when the fan 44 is activated or rotated, air is drawn into the cavity 24, around the internal components, through filter media 66 and then "filtered air is propelled out the shroud 42 of the fan assembly 40. Those skilled in the art will appreciate that at times it may be desirable to reverse the rotation direction of the fan such that air is drawn by the fan and propelled through the filter media 66, into the internal cavity 24 and out ports extending through the housing 20.

Referring next to FIGS. 4-11, various components of the headlamp apparatus 10 will be described in further detail. Housing 20 of the headlamp 10 contains a replaceable fan assembly 40, a primary PCBA 16, replaceable filter assembly 60, primary heat sink 80, secondary heat sink 84, and light assembly 100 within the cavity 24 of the housing. The light assembly 100 is aligned along longitudinal or central axis 30 and is centered with the light emitting opening 26. Replaceable fan assembly includes a low voltage fan 44 of known suitable construction and a ported shroud 42 that covers and inlet/outlet of the housing 20. Filter assembly includes a bottom tray 62 and top tray 64 that traps a filter media 66 between the two trays. The trays may include apertures or a framework that allows air to pass through the trays while providing support to the filter media. Primary heat sink 80 is thermally engaged to secondary heat sink 84 at mounting surface 88. The primary heat sink 80 includes fins 82 and the secondary heat sink includes fins 86 that together facilitate heat or thermal dissipation. Primary PCBA 16 is electrically coupled to power cable 14. The PCBA 16 is further electrically coupled to fan 44 and LED assembly 100 to provide electrical power and control to the same.

Components of light assembly 100 are generally contained by containment member or cam barrel 130 and are further enclosed by front barrel 180 and primary heat sink 80. LED 108 is mounted to a copper PCBA 104 and centrally aligned with an aperture extending through lens holder 112. Threaded ring 114 threads onto lens holder 112 and mounts to the PCBA 104 with fasteners 90. The lens holder 112 retains first condenser lens 116, spacer 118, and second condenser lens 120. Spacer 118 retains condenser lens 116 in alignment within the lens holder 112. Spacer 124 is positioned between the lens holder 112 and iris 150. The spacer retains condenser lens 120 in alignment within the lens holder 112. Iris 150 includes and adjustable aperture of known suitable construction. A rotation of peg 154 about the longitudinal axis 30 of the housing 20 enlarges or reduces the diameter of the aperture 152 of the iris 150, dependent upon the direction of rotation. Peg 154 engages within slot 136 formed in cam barrel 134. Lens holder 158 retains lens 162 within the holder and aligned adjacent the aperture of the iris 150. A peg 160 or other member extends outward from holder 158 and engages within slot 138 formed in the cam barrel 134. A rotating link 142 further engages pegs 154 and 160. Threaded ring 166 secures lens 162 to the lens holder 158. Front barrel 180 is secured to cam barrel or containment member 134. Spacer 184 retains fourth lens 188 within front barrel 180 and in alignment with the central axis 30.

FIGS. 12-15 further illustrates features of portions of the light assembly 100. Rotating link member 142 further includes a post 144 that extends outward from the link member. The post 144 engages a coupler 148 formed in the inner side of the adjusting ring 146. In use, when the adjusting ring 146 is rotated, the rotating link engages the pegs 154 and 160 thereby moving the pegs within corresponding slots 136 and 138 of the cam barrel. Movement of peg 154 enlarges and reduces the aperture 152 of iris 150. Simultaneous movement of peg 160 linearly actuates lens holder 158 and lens 162. Thus, continuous enlarging of a diameter of an aperture 152 of the iris 150 continuously, linearly actuates the lens 162 away from the iris 150 and continuously reducing the diameter of the aperture 152 of the iris 150 continuously, linearly actuates the lens 162 towards the iris 150. In this manner, the user may adjust the spot size of the illuminating light beam while the lens 162 reduces degradation of the brightness of the light beam.

These and various other aspects and features of the invention are described with the intent to be illustrative, and not restrictive. This invention has been described herein with detail in order to comply with the patent statutes and to provide those skilled in the art with information needed to apply the novel principles and to construct and use such specialized components as are required. It is to be understood, however, that the invention can be carried out by specifically different constructions, and that various modifications, both as to the construction and operating procedures, can be accomplished without departing from the scope of the invention. Further, in the appended claims, the transitional terms comprising and including are used in the open-ended sense in that elements in addition to those enumerated may also be present. Other examples will be apparent to those of skill in the art upon reviewing this document.

The following claims are incorporated into this description.

The invention claimed is:

1. An apparatus to provide sanitary control of a health care provider's headlamp, the apparatus comprising:
 a headlamp housing having an interior cavity adapted to contain components of the headlamp, the headlamp housing further having a light emitting opening extending from an outer surface of the headlamp housing into the interior cavity, and the headlamp housing further having a longitudinal axis extending through the housing and aligned with a center of the central opening;
 a light assembly contained within the interior cavity of the headlamp housing, the light assembly having a length axis aligned parallel with the longitudinal axis of the housing;
 the light assembly further having a light source aligned along the length axis of the light assembly, a first condenser lens aligned along the length axis of the light assembly adjacent the light source, and a second condenser lens aligned along the length axis of the light assembly and aligned proximate the first condenser lens wherein a spacer is aligned along the length axis of the light assembly and positioned between the first condenser lens and second condenser lens;
 the light assembly further having a containment member aligned along the length axis of the light assembly wherein the containment member has an iris member contained therein having an adjustable aperture contained therein and further wherein the containment member has a linearly actuatable lens contained therein; and
 the light assembly further having a front lens aligned along the length axis of the light assembly proximate both the linearly actuatable lens and the central opening of the housing.

2. The apparatus as recited in claim 1, wherein the light source includes a PCBA for a light emitting diode (LED).

3. The apparatus as recited in claim 2, further including a primary heat sink and secondary heat sink thermally coupled to the LED, wherein both the primary heat sink and secondary heat sink are contained within the internal cavity of the headlamp housing.

4. The apparatus as recited in claim 3, further including a replaceable fan adapted for circulating air within the interior cavity of the headlamp housing.

5. The apparatus as recited in claim 4, further including a removable filter assembly coupled between the fan and a main portion of the interior cavity of the headlamp housing.

6. The apparatus as recited in claim 4, wherein the headlamp housing has a plurality of ports extending from the outer surface of the headlamp housing into the internal cavity, wherein the plurality of ports are adapted for transmitting vapors into the internal cavity of the headlamp housing wherein the vapors are suitable for cleaning components contained within the internal cavity of the headlamp housing.

7. The apparatus as recited in claim 5, wherein the filter includes a thumb tab that extends from an external surface of the headlamp housing.

8. The apparatus as recited in claim 5, wherein the filter consists of a scented pad capable of filtering particulate having a size greater than 0.3 microns.

9. The apparatus as recited in claim 1, wherein the containment member includes an actuator that reduces and increases a diameter of the aperture of the iris in proportion to a distance the moveable lens actuates linearly.

10. An apparatus to provide sanitary control of a health care provider's headlamp, the apparatus comprising:
- a headlamp housing having an interior cavity adapted to contain components of the headlamp, the headlamp housing further having a light emitting opening extending from an outer surface of the headlamp housing into the interior cavity, and the headlamp housing further having a longitudinal axis extending through the housing and aligned with a center of the central opening;
- a fan adapted for circulating air within the interior cavity of the headlamp housing;
- a removable filter assembly coupled between the fan and a main portion of the interior cavity of the headlamp housing;
- a light assembly contained within the interior cavity of the headlamp housing, the light assembly having a length axis aligned parallel with the longitudinal axis of the housing;
- the light assembly further having an LED aligned along the length axis of the light assembly, a first condenser lens aligned along the length axis of the light assembly adjacent the LED, a second condenser lens aligned along the length axis of the light assembly axially proximate the first condenser lens wherein a spacer is aligned along the length axis of the light assembly and positioned between the first condenser lens and second condenser lens;
- the light assembly further having a containment member aligned along the length axis of the light assembly wherein the containment member has an iris member having an adjustable aperture contained therein and further wherein the containment member has a linearly actuatable lens contained therein; and
- the light assembly further having a front lens aligned along the length axis of the light assembly proximate both the linearly actuatable lens and the central opening of the housing.

11. The apparatus as recited in claim 10, wherein the LED includes a copper PCBA for the LED.

12. The apparatus as recited in claim 10, further including a primary heat sink and secondary heat sink thermally coupled to the LED, wherein both the primary heat sink and secondary heat sink are contained within the internal cavity of the headlamp housing.

13. The apparatus as recited in claim 10, wherein the headlamp housing has a plurality of ports extending from the outer surface of the headlamp housing into the internal cavity, wherein the plurality of ports are adapted for transmitting vapors into the internal cavity of the headlamp housing wherein the vapors are suitable for cleaning components contained within the internal cavity of the headlamp housing.

14. The apparatus as recited in claim 10, wherein the filter includes a thumb tab that extends from an external surface of the headlamp housing.

15. The apparatus as recited in claim 10, wherein the filter consists of a scented pad capable of filtering particulate having a size greater than 0.3 microns.

16. The apparatus as recited in claim 10, wherein the containment member includes an actuator that reduces and increases a diameter of the aperture of the iris in proportion to a distance the moveable lens actuates linearly.

17. A method of sanitizing a health care provider's headlamp, the method comprising the steps of:
- providing a headlamp having an adjustable light beam and having a cooling mechanism, the headlamp including:
  - a headlamp housing having an interior cavity adapted to contain components of the headlamp, the headlamp housing further having a light emitting opening extending from an outer surface of the headlamp housing into the interior cavity, and the headlamp housing further having a longitudinal axis extending through the housing and aligned with a center of the central opening;
  - a fan adapted for circulating air within the interior cavity of the headlamp housing;
  - a removable filter assembly coupled between the fan and a main portion of the interior cavity of the headlamp housing;
  - a light assembly contained within the interior cavity of the headlamp housing, the light assembly having a length axis aligned parallel with the longitudinal axis of the housing;
  - the light assembly further having an LED aligned along the length axis of the light assembly, a first condenser lens aligned along the length axis of the light assembly adjacent the LED, a second condenser lens aligned along the length axis of the light assembly axially proximate the first condenser lens wherein a spacer is aligned along the length axis of the light assembly and positioned between the first condenser lens and second condenser lens;
  - the light assembly further having a containment member aligned along the length axis of the light assembly wherein the containment member has an iris member having an adjustable aperture contained therein and further wherein the containment member has a linearly actuatable lens contained therein; and
  - the light assembly further having a front lens aligned along the length axis of the light assembly proximate both the linearly actuatable lens and the central opening of the housing.

18. The method as recited in claim 17, further wherein the headlamp housing has a plurality of ports extending from the outer surface of the headlamp housing into the internal cavity, wherein the plurality of ports are adapted for infusing vapors into the internal cavity of the headlamp housing.

19. The method as recited in claim 18, further including the step of infusing an anti-microbial vapor through the plurality of ports.

20. The method as recited in claim 19, further including the step of inserting a filter consisting of a scented pad capable of filtering particulate having a size greater than 0.3 microns into the removable filter assembly.

* * * * *